(12) United States Patent
Jaehne et al.

(10) Patent No.: US 6,235,763 B1
(45) Date of Patent: May 22, 2001

(54) POLYCYCLIC 2-AMINODIHYDROTHIAZOLE SYSTEMS, PROCESSES FOR THEIR PREPARATION AND THEIR USE AS PHARMACEUTICALS

(75) Inventors: Gerhard Jaehne; Karl Geisen, both of Frankfurt; Hans-Jochen Lang, Hofheim; Martin Bickel, Bad Homburg, all of (DE)

(73) Assignee: Aventis Pharma Deutschland GmbH, Frankfurt am Main (DE)

(*) Notice: Subject to any disclaimer, the term of this patent is extended or adjusted under 35 U.S.C. 154(b) by 0 days.

(21) Appl. No.: 09/499,350

(22) Filed: Feb. 8, 2000

(30) Foreign Application Priority Data

Feb. 26, 1999 (DE) .............................. 199 08 539

(51) Int. Cl.⁷ .......................... A61K 31/381; A61P 3/04; C07D 277/60
(52) U.S. Cl. .............................. 514/366; 548/150
(58) Field of Search ................... 514/366; 548/150

(56) References Cited

U.S. PATENT DOCUMENTS

| | | | |
|---|---|---|---|
| 3,507,868 | 4/1970 | Manning | 260/251 |
| 4,129,656 | 12/1978 | Lang et al. | 424/263 |
| 4,164,579 * | 8/1979 | Bourzat et al. | 424/263 |
| 4,174,397 | 11/1979 | Knabe et al. | 424/270 |
| 4,208,420 | 6/1980 | Maillard et al. | 424/270 |
| 5,834,499 * | 11/1998 | Iwoaka et al. | 514/366 |
| 6,090,833 * | 7/2000 | Jaehne et al. | 514/366 |

FOREIGN PATENT DOCUMENTS

| | | |
|---|---|---|
| 365181 | 12/1981 | (AT) . |
| 507290 | 5/1971 | (CH) . |
| 26 01 791 | 7/1977 | (DE) . |
| 26 40 358 | 3/1978 | (DE) . |
| 28 45 857 | 4/1979 | (DE) . |

OTHER PUBLICATIONS

O. Mitsunobu, "The Use of Diethyl Azodicarboxylate and Triphenylphosphine in Synthesis and Transformation of Natural Products.", Synthesis, Jan. 1981, pp. 1–28.

P. Tyle, "Iontophoretic Devices for Drug Delivery", Pharmaceutical Research, 1986, 3 (6): pp. 318–326.

* cited by examiner

Primary Examiner—Deborah C. Lambkin
Assistant Examiner—Sonya N. Wright
(74) Attorney, Agent, or Firm—Heller Ehrman White & McAuliffe LLP

(57) ABSTRACT

The invention relates to polycyclc 2-aminodihydrothiazole systems and their physiologically tolerated salts and physiologically functional derivatives. Compounds of the formula I,

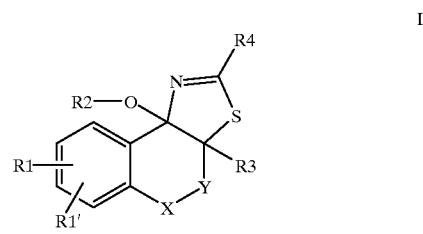

in which the radicals have the stated meanings, and their physiologically tolerated salts and processes for their preparation are described. The compounds are suitable, for example, as anorectics.

24 Claims, No Drawings

POLYCYCLIC 2-AMINODIHYDROTHIAZOLE SYSTEMS, PROCESSES FOR THEIR PREPARATION AND THEIR USE AS PHARMACEUTICALS

BACKGROUND OF THE INVENTION

Polycyclic 2-aminodihydrothiazole systems, processes for their preparation and their use as pharmaceuticals.

The invention relates to polycyclic 2-aminodihydrothiazole systems and their physiologically tolerated salts and physiologically functional derivatives. Thiazolidine derivatives having an anorectic effect are described in the prior art (Austrian Patent No. 365181).

The invention was based on the object of providing further compounds which display a therapeutically utilizable anorectic effect.

SUMMARY OF THE INVENTION

The invention relates to compounds of the formula I

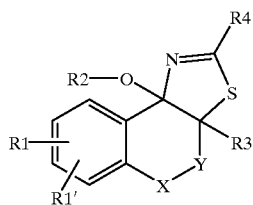

I in which
Y is a direct linkage, —$CH_2$— or —$CH_2$—$CH_2$—;
X is $CH_2$, $CH(CH_3)$, $CH(C_2H_5)$, $CH(C_3H_7)$ or $CH(C_6H_5)$;
R1, R1' are independently H, F, Cl, Br, I, $CF_3$, $NO_2$, CN, COOH, COO($C_1$–$C_6$)-alkl, $CONH_2$, CONH($C_1$–$C_6$) alkyl, CON[($C_1$–$C_6$)alkyl]$_2$, ($C_1$–$C_6$)-alkyl, ($C_2$–$C_6$)-alkenyl, ($C_2$–$C_6$)-alkynyl, O-($C_1$–$C_6$)-alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, NH—CO—$CH_3$ or N(COOCH$_2$Ph)$_2$), $SO_2$—$NH_2$, $SO_2$NH($C_1$–$C_6$)-alkyl, $SO_2$N[($C_1$–$C_6$)-akyl]$_2$, S—($C_1$–$C_6$)-alkyl, S—($CH_2$)$_n$-phenyl, SO-($C_1$–$C_6$)-alkyl, SO—($CH_2$)$_n$-phenyl, $SO_2$—($C_1$–$C_6$)-alkyl, $SO_2$—($CH_2$)$_n$-phenyl (where n is 0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$), $NH_2$, NH—($C_1$–$C_6$)-alkyl, N(($C_1$–$C_6$)-alkyl)$_2$, NH($C_1$–$C_7$)-acyl, phenyl, biphenylyl, O—($CH_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position 1 or 2 by methyl or benzyl);
R2 is H, ($C_1$–$C_6$)alkyl, ($C_3$–$C_6$)-cycloalkyl, ($CH_2$)$_n$-phenyl, ($CH_2$)$_n$-thienyl, ($CH_2$)$_n$-pyridyl, ($CH_2$)$_n$-furyl, C(O)—($C_1$–$C_6$)-alkyl, C(O)—($C_3$–$C_6$)-cycloalkyl, C(O)—($CH_2$)$_n$-phenyl, C(O)—($CH_2$)$_n$-thienyl, C(O)—($CH_2$)$_n$-pyridyl or C(O)—($CH_2$)$_n$-furyl (where n is 0–5 and wherein phenyl, thienyl, pyridyl, furyl may be substituted up to two times by Cl, F, CN, $CF_3$, ($C_1$–$C_3$)-alkyl, OH or O—($C_1$–$C_6$)-alkyl);
R3 is H, ($C_1$–$C_6$)-alkyl, F, CN, $N_3$, O—($C_1$–$C_6$)-alkyl, ($CH_2$)$_n$-phenyl, ($CH_2$)$_n$-thienyl, ($CH_2$)$_n$-pyridyl, ($CH_2$)$_n$-furyl (where n is 0–5 and wherein phenyl, thienyl, pyridyl, furyl may each be substituted up to two times by Cl, F, CN, $CF_3$, ($C_1$–$C_3$)-alkyl, OH or O—($C_1$–$C_6$)-alkyl), ($C_2$–$C_6$)-alkynyl, ($C_2$–$C_6$)-alkenyl, C(O)OCH$_3$, C(O)OCH$_2$CH$_3$, C(O)OH, C(O)NH$_2$, C(O)NHCH$_3$, C(O)N(CH$_3$)$_2$ or OC(O)CH$_3$;
R4 is NR6R7;
R6 and R7 are independently H, ($C_1$–$C_6$)-alkyl, ($C_3$–$C_6$)-cycloalkyl, phenyl (wherein the phenyl ring may be optionally substituted up to two times by Cl, F, CN, $CF_3$, ($C_1$–$C_3$)-alkyl, OH or O—($C_1$–$C_6$)-alkyl)), CO—($C_1$–$C_6$)-alkyl, CHO, CO-phenyl, —$NH_2$, —N=C(CH$_3$)$_2$, -(pyrrolidin-1-yl), -(piperidin-1-yl), -(morpholin4-yl), -(piperazin-1-yl) or -(4-methylpiperazin- 1 -yl), or NR6R7 is a ring selected from the group consisting of pyrrolidine, piperidine, morpholine, piperazine, 4-methylpiperazin-1-yl, 4-benzylpiperazin-1-yl and phthalimidyl;
and their physiologically tolerated salts and physiologically functional derivatives.

The invention also relates to pharmaceutical compositions containing the compounds of formula I and pharmaceutically acceptable carriers. Also pharmaceutical compositions containing the compounds of formula I in combination with at least one additional anorectic agents are contemplated. The invention envisages treatment of obesity via administration of compounds of formula I. Methods of treatment for type II diabetes are also contemplated.

DETAILED DESCRIPTION OF THE PREFERRED EMBODIMENTS

The invention encompasses compounds of formula I

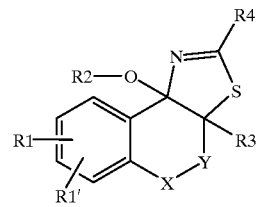

I in which
Y is a direct linkage, —$CH_2$— or —$CH_2$—$CH_2$—;
X is $CH_2$, $CH(CH_3)$, $CH(C_2H_5)$, $CH(C_3H_7)$ or $CH(C_6H_5)$;
R1, R1' are independently H, F, Cl, Br, I, $CF_3$, $NO_2$, CN, COOH, COO($C_1$–$C_6$)alkyl, $CONH_2$, CONH($C_1$–$C_6$)alkyl, CON[($C_1$–$C_6$)alkyl]$_2$, ($C_1$–$C_6$)-alkyl, ($C_2$–$C_6$)-alkenyl, ($C_2$–$C_6$)-alkynyl, O—($C_1$–$C_6$)-alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, NH—CO—$CH_3$ or N(COOCH$_2$Ph)$_2$), $SO_2$—$NH_2$, $SO_2$NH($C_1$–$C_6$)-alkyl, $SO_2$N[($C_1$–$C_6$)-alkyl]$_2$, S—($C_1$–$C_6$)-alkyl, S—($CH_2$)$_n$-phenyl, SO—($C_1$–$C_6$)-alkyl, SO-($CH_2$)$_n$-phenyl, $SO_2$—($C_1$–$C_6$)-alkyl, $SO_2$—($CH_2$)$_n$-phenyl (where n is 0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$), $NH_2$, NH—($C_1$–$C_6$)-alkyl, N(($C_1$–$C_6$)-alkyl)$_2$, NH($C_1$–$C_7$)-acyl, phenyl, biphenylyl, O—($CH_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, $CF_3$, $NO_2$, CN, $OCF_3$, O—$(C_1-C_6)$-alkyl, $(C_1-C_6)$-alkyl, $NH_2$, NH$(C_1-C_6)$-alkyl, N$((C_1-C_6)$-alkyl$)_2$, $SO_2$—$CH_3$, COOH, COO—$(C_1-C_6)$-alkyl or $CONH_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position 1 or 2 by methyl or benzyl);

R2 is H, $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, C(O)—$(C_1-C_6)$-alkyl, C(O)—$(C_3-C_6)$-cycloalkyl, C(O)—$(CH_2)_n$-phenyl, C(O)—$(CH_2)_n$-thienyl, C(O)—$(CH_2)_n$-pyridyl or C(O)—$(CH_2)_n$-furyl (where n is 0–5 and wherein phenyl, thienyl, pyridyl, furyl may be substituted up to two times by Cl, F, CN, $CF_3$, $(C_1-C_3)$-alkyl, OH or O—$(C_1-C_6)$-alkyl);

R3 is H, (CI-C6)-alkyl, F, CN, N3, O-(Ci-C6)-alkyl, $(CH_2)_n$-phenyl, $(CH_2)_n$-thienyl, $(CH_2)_n$-pyridyl, $(CH_2)_n$-furyl (where n is 0–5 and wherein phenyl, thienyl, pyridyl, furyl may each be substituted up to two times by Cl, F, CN, $CF_3$, $(C_1-C_3)$-alkyl, OH or O—$(C_1-C_6)$-alkyl), $(C_2-C_6)$-alkynyl, $(C_2-C_6)$-alkenyl, $C(O)OCH_3$, $C(O)OCH_2CH_3$, C(O)OH, $C(O)NH_2$, $C(O)NHCH_3$, $C(O)N(CH_3)_2$ or $OC(O)CH_3$;

R4 is NR6R7;

R6 and R7 are independently H, $(C_1-C_6)$-alkyl, $(C_3-C_6)$-cycloalkyl, phenyl (wherein the phenyl ring may be optionally substituted up to two times by Cl, F, CN, $CF_3$, $(C_1-C_3)$-alkyl, OH or O—$(C_1-C_6)$-alkyl)), CO—$(C_1-C_6)$-alkyl, CHO, CO-phenyl, —$NH_2$, —N=$C(CH_3)_2$, -(pyrrolidin-1-yl), -(piperidin-1-yl), -(morpholin4-yl), -(piperazin-1-yl) or -(4-methylpiperazin-1-yl), or $NR_6R_7$ is a ring selected from the group consisting of pyrrolidine, piperidine, morpholine, piperazine, 4-methylpiperazin-1-yl, 4-benzylpiperazin-1-yl and phthalimidyl;

and their physiologically tolerated salts and physiologically functional derivatives.

In a preferred embodiment are compounds of formula I: in which

Y is a direct linkage;

X is $CH_2$;

R1, R1' are independently H, F, Cl, $CF_3$, $NO_2$, CN, COOH, COO$(C_1-C_6)$alkyl, $CONH_2$, CONH$(C_1-C_6)$alkyl, CON$[(C_1-C_6)$alkyl$]_2$, $(C_1-C_6)$-alkyl, $(C_2-C_6)$-alkenyl, $(C_2-C_6)$-alkynyl, O—$(C_1-C_6)$-alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, NH—CO—$CH_3$ or $N(COOCH_2Ph)_2)$, $SO_2$—$NH_2$, $SO_2$NH$(C_1-C_6)$-alkyl, $SO_2N[(C_1-C_6)$-alkyl$]_2$, $SO_2$—$(C_1-C_6)$-alkyl, $SO_2$—$(CH_2)_n$-phenyl (where n is 0–6 and the phenyl radical may be substituted by F, Cl, Br, OH, $CF_3$, $NO_2$, CN, $OCF_3$, O—$(C_1-C_6)$-alkyl, $(C_1-C_6)$-alkyl or $NH_2$), $NH_2$, NH—$(C_1-C_6)$-alkyl, N$((C_1-C_6)$-alkyl$)_2$, NH$(C_1-C_7)$-acyl, phenyl, biphenylyl, O—$(CH_2)_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted once or twice by F, Cl, Br, I, OH, $CF_3$, $NO_2$, CN, $OCF_3$, O—$(C_1-C_6)$-alkyl, $(C_1-C_6)$-alkyl, $NH_2$, NH$(C_1-C_6)$-alkyl, N$((C_1-C_6)$-alkyl$)_2$, $SO_2$—$CH_3$, COOH, COO—$(C_1-C_6)$-alkyl or $CONH_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R2 is H, $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, C(O)—$(C_1-C_6)$-alkyl, C(O)—$(C_3-C_6)$-cycloalkyl, C(O)—$(CH_2)_n$-phenyl, C(O)—$(CH_2)_n$-thienyl, C(O)—$(CH_2)_n$-pyridyl or C(O)—$(CH_2)_n$-furyl (where n is 0–5 and wherein phenyl, thienyl, pyridyl, furyl may each be substituted up to two times by Cl, F, CN, $CF_3$, $(C_1-C_3)$-alkyl, OH or O—$(C_1-C_6)$-alkyl);

R3 is H, $(C_1-C_6)$-alkyl, F, $(CH_2)_n$-phenyl, $(CH_2)_n$-thienyl, $(CH_2)_n$-pyridyl, $(CH_2)_n$-furyl (where n is 0–5 and wherein phenyl, thienyl, pyridyl, furyl may each be substituted up to two times by Cl, F, CN, $CF_3$, $(C_1-C_3)$-alkyl, OH or O—$(C_1-C_6)$-alkyl), $(C_2-C_6)$-alkynyl, $(C_2-C_6)$-alkenyl, $C(O)OCH_3$, $C(O)OCH_2CH_3$, C(O)OH, $C(O)NH_2$, $C(O)NHCH_3$, $C(O)N(CH_3)_2$ or $OC(O)CH_3$);

R4 is NR6R7;

R6 and R7 are independently H, $(C_1-C_6)$-alkyl, $(C_3-C_6)$-cycloalkyl, phenyl (wherein the phenyl ring may be optionally substituted up to two times by Cl, F, CN, $CF_3$, $(C_1-C_3)$-alkyl, OH or O—$(C_1-C_6)$-alkyl), CO—$(C_1-C_6)$-alkyl, CHO, CO-phenyl, —$NH_2$, —N=$C(CH_3)_2$, -(pyrrolidin-1-yl), -(piperidin-1-yl), -(morpholin-4-yl), -(piperazin-1-yl) or -(4-methylpiperazin-1-yl), $NR_6R_7$ is a ring selected from the group consisting of pyrrolidine, piperidine, morpholine, piperazine, 4-methylpiperazin-1-yl, 4-benzylpiperazin-1-yl and phthalimidyl;

and their physiologically tolerated salts and physiologically functional derivatives.

In a particularly preferred embodiment are compounds of formula I wherein:

Y is a direct linkage;

X is $CH_2$;

R1, R1' are independently H, F, Cl, $CF_3$, CN, COOH, COO$(C_1-C_6)$alkyl, $CONH_2$, CONH$(C_1-C_6)$alkyl, CON$[(C_1-C_6)$alkyl$]_2$, $(C_1-C_6)$-alkyl, $(C_2-C_6)$-alkenyl, $(C_2-C_6)$-alkynyl, O—$(C_1-C_6)$-alkyl (where one, more than one or all hydrogen(s) in the alkyl radicals may be replaced by fluorine, or one hydrogen may be replaced by OH, OC(O)$CH_3$, OC(O)H, O—$CH_2$—Ph, $NH_2$, NH—CO—$CH_3$ or $N(COOCH_2Ph)_2)$, $SO_2$—$(C_1-C_6)$-alkyl, $SO_2$—$(CH_2)_n$-phenyl (where n is 0–3 and the phenyl radical may be substituted by F, Cl, OH, $CF_3$, CN, $OCF_3$, O—$(C_1-C_6)$-alkyl, $(C_1-C_6)$-alkyl or $NH_2$), $NH_2$, NH—$(C_1-C_6)$-alkyl, N$((C_1-C_6)$-alkyl$)_2$, NH$(C_1-C_7)$-acyl, phenyl, biphenylyl, O—$(CH_2)_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted once or twice by F, Cl, OH, $CF_3$, CN, $OCF_3$, O—$(C_1-C_4)$-alkyl, $(C_1-C_4)$-alkyl, $NH_2$, NH$(C_1-C_4)$-alkyl, N$((C_1-C_4)$-alkyl$)_2$, $SO_2$—$CH_3$, COOH, COO—$(C_1-C_4)$-alkyl or $CONH_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R2 is H, $(C_1-C_6)$-alkyl, $(CH_2)_n$-phenyl, $(CH_2)_n$-thienyl, $(CH_2)_n$-pyridyl or $(CH_2)_n$-furyl (wherein phenyl, thienyl, pyridyl, furyl may be substituted up to two times by Cl, F, CN, $CF_3$, $(C_1-C_3)$-alkyl, OH or O—$(C_1-C_6)$-alkyl);

R3 is H, F or $(C_1-C_4)$-alkyl;

R4 is NR6R7;

R6 and R7 are independently H, $(C_1-C_6)$-alkyl, $(C_3-C_6)$-cycloalkyl, phenyl (wherein the phenyl ring may be optionally substituted up to two times by Cl, F, CN, $CF_3$, $(C_1-C_3)$-alkyl, OH or O—$(C_1-C_6)$-alkyl), CO—$(C_1-C_6)$-alkyl, CHO, CO-phenyl, —$NH_2$, —N=$C(CH_3)_2$, -(pyrrolidin-1- yl), -(piperidin-1-yl), -(morpholin-4-yl), -(piperazin-1-yl) or -(4-methylpiperazin-1-yl), NR6R7 is a ring selected from the group consisting of pyrrolidine, piperidine, morpholine, piperazine, 4-methylpiperazin-1-yl, 4-benzylpiperazin-1-yl and phthalimidyl;

and their physiologically tolerated salts.

The invention also relates to compounds of the formula I in the form of their racemates, racemic mixtures and pure enantiomers, and to their diastereomers and mixtures thereof.

The alkyl, alkenyl and alkynyl radicals in the substituents R1, R1', R2, R3, R4, R6 and R7 may be either straight-chain or branched.

Pharmaceutically acceptable salts are particularly suitable for medical applications because of their greater solubility in water compared with the initial compounds on which they are based. These salts must have a pharmaceutically acceptable anion or cation. Suitable pharmaceutically acceptable acid addition salts of the compounds of the invention are salts of inorganic acids such as hydrochloric acid, hydrobromic acid, phosphoric, metaphosphoric, nitric and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids. It is particularly preferred to use the chloride for medical purposes. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise fall within the scope of the invention as useful intermediates for preparing or purifying pharmaceutically acceptable salts and/or for use in non-therapeutic, for example in vitro, applications.

The term "physiologically functional derivative" used herein refers to any physiologically tolerated derivative of a compound of the formula I according to the invention, for example an ester, which is able on administration to a mammal, such as, for example, to humans, to form (directly or indirectly) a compound of the formula I or an active metabolite thereof.

The physiologically functional derivatives also include prodrugs of compounds of the invention. Such prodrugs may be metabolized in vivo to a compound of the invention. These prodrugs may themselves be active or not. The compounds of the invention may also exist in various polymorphous forms, for example as amorphous and crystalline polymorphous forms. All polymorphous forms of the compounds of the invention fall within the scope of the invention and are a further aspect of the invention.

All references hereinafter to "compound(s) of the formula (I)" refer to compound(s) of the formula (I) as described above and to the salts, solvates and physiologically functional derivatives thereof as described herein.

The compounds of formula (I) are useful in the treatment of type II diabetes and in the treatment of obesity. Treatment includes either the prophylaxis or the amelioration of the disorder. In order to achieve the treatment, an effective amount of a compound of formula (I) is administered to a patient in need thereof. An "effective amount" is the amount which achieves the treatment of the specified state.

The amount of a compound of the formula (I), which is an "effective amount," that is necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram body weight, for example 3–10 mg/kg/day. An intravenous dose may be, for example, in the range from 0.3 mg to 1.0 mg/kg, which may suitably be administered as infusion of 10 ng to 100 ng per kilogram and per minute. Infusion solutions suitable for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single dose formulations which may be administered orally, such as, for example, tablets or capsules, may contain, for example, from 1.0 to 1000 mg, typically from 10 to 600 mg. In the case of pharmaceutically acceptable salts, the above weight data are based on the weight of the dihydrothiazolium ion derived from the salt. The compounds of the formula (I) may be used in treatment of obesity and type II diabetes in the form of a compound itself, but they are preferably in the form of a pharmaceutical composition with a pharmaceutically acceptable carrier. The carrier must, of course, be compatible in the sense of compatibility with other ingredients of the composition and not be harmful to the patient's health. The carrier may be a solid or a liquid or both and is preferably formulated with the compound as single dose, for example as tablet, which may contain from 0.05% to 95% by weight of the active ingredient. Further pharmaceutically active substances may likewise be present, including further compounds of the formula (I). The pharmaceutical compositions according to the invention may be produced by one of the known pharmaceutical methods which essentially consists of mixing the ingredients with pharmacologically acceptable carriers and/or excipients.

Pharmaceutical compositions according to the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of the formula (I) used in each case. Coated formulations and coated slow-release formulations also fall within the scope of the invention. Acid- and gastric fluid-resistant formulations are preferred. Suitable gastric fluid-resistant coatings comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, pastilles or tablets, each of which contains a defmed amount of the compound of the formula (I); as powder or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are produced by uniform and homogeneous mixing of the active ingredient with a liquid and/or fmely dispersed solid carrier, after which the product is shaped if necessary. Thus, for example, a tablet may be produced by compressing or shaping the powder or granules of the compound, where appropriate with one or more additional ingredients. Compressed tablets may be produced by tabletting the compound in free-flowing form, such as, for example, a powder or granules, where appropriate mixed with a binder, lubricant, inert diluent and/or one (or more) surface-active/dispersing agents in a suitable machine. Shaped tablets may be produced by shaping, in a suitable machine, the compound which is in powder form and has been moistened with an inert liquid diluent.

Pharmaceutical compositions suitable for peroral (sublingual) administration comprise suckable tablets which contain a compound of the formula (I) with a flavoring, normally sucrose, and gum arabic or tragamayth, and pastilles which contain the compound in an inert base such as gelatin and glycerol or sucrose and gum arabic.

Suitable pharmaceutical compositions for parenteral administration comprise preferably sterile aqueous preparations of a compound of the formula (I), which are preferably isotonic with the blood of the intended recipient. These preparations are preferably administered intravenously, although administration may also take place by subcutaneous, intramuscular or intradermal injection. These preparations may preferably be produced by mixing the compound with water and making the resulting solution sterile and isotonic with blood. Injectable compositions according to the invention generally contain from 0.1 to 5% by weight of the active compound.

Suitable pharmaceutical compositions for rectal administration are preferably in the form of single-dose suppositories. These may be produced by mixing a compound of the formula (I) with one or more conventional solid carriers, for example cocoa butter, and shaping the resulting mixture.

Suitable pharmaceutical compositions for topical use on the skin are preferably in the form of an ointment, cream, lotion, paste, spray, aerosol or oil. Carriers which may be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Suitable pharmaceutical compositions for transdermal applications may be in the form of single plasters which are suitable for long-term close contact with the patient's epidermis. Plasters of this type suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. As a particular option, the active ingredient may be released by electrotransport or iontophoresis as described, for example, in Pharmaceutical Research, 2(6):318 (1986).

The invention further relates to a process for preparing the compounds of the formula I, which comprises obtaining the compounds of the formula I by the procedure as shown in the following reaction scheme:

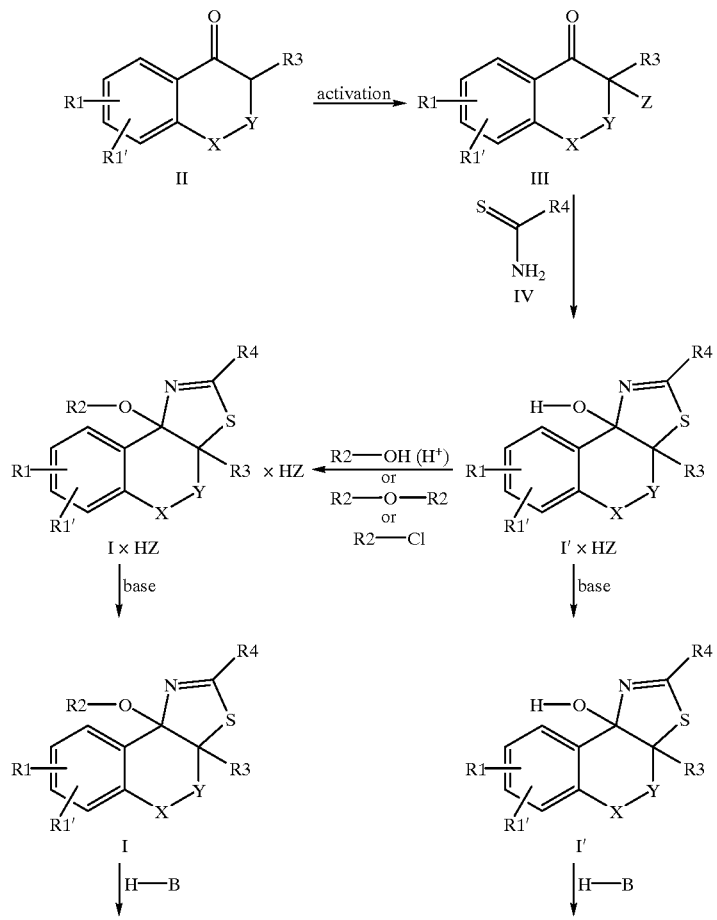

-continued

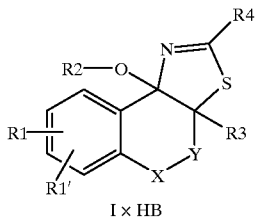

I × HB

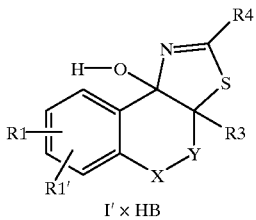

I' × HB

For this purpose, compounds of the formula II,

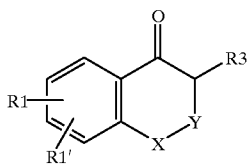

Formula II in which R1, R1', R3 and X and Y have the stated meaning, are activated and converted into a compound of the formula III in which Z is the residue of an activated ester of an inorganic or organic acid.

The compounds of the formula III are reacted further with thioureas of the formula IV

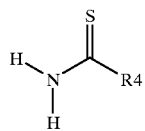

IV in which R4 has the stated meaning, to give compounds of the formula I'×HZ or I', converting where appropriate the compounds of the formula I' with organic or inorganic acids H—B into their acid addition salts of the formula I'×HB or converting salts obtained of the formula I'×HZ with organic or inorganic bases into the free basic compounds of the formula I'.

Examples of suitable inorganic acids are: hydrohalic acids such as hydrochloric acid and hydrobromic acid, and sulfuric acid, phosphoric acid and sulfamic acid.

Examples of organic acids which may be mentioned are: formic acid, acetic acid, benzoic acid, p-toluenesulfonic acid, benzenesulfonic acid, succinic acid, fumaric acid, maleic acid, lactic acid, tartaric acid, citric acid, L-ascorbic acid, salicylic acid, isethionic acid, methanesulfonic acid, trifluoromethanesulfonic acid, 1,2-benzisothiazol-3(2H)-one, 6-methyl-1,2,3-oxathiazin-4(3H)-one 2,2-dioxide. The procedure described above is advantageously carried out by reacting the compounds m with the thioureas IV in the molar ratio of from 1:1 to 1:1.5. The reaction is advantageously carried out in an inert solvent, for example in polar organic solvents such as dimethylformamide, dimethylacetamide, N-methyl-2-pyrrolidone, dioxane, tetrahydrofuran, acetonitrile, nitromethane or diethylene glycol dimethyl ether. However, solvents which prove to be particularly advantageous are methyl acetate and ethyl acetate, short-chain alcohols such as methanol, ethanol, propanol, isopropanol, and lower dialkyl ketones such as, for example, acetone, 2-butanone or 2-hexanone. It is also possible to use mixtures of the reaction media mentioned; thus, it is also possible to use mixtures of the solvents mentioned with solvents which are less suitable on their own, such as, for example, mixtures of methanol with benzene, ethanol with toluene, methanol with diethyl ether or with tert-butyl methyl ether, ethanol with tetrachloromethane, acetone with chloroform, dichloromethane or 1,2-dichloroethane, it being expedient for the more polar solvent in each case to be used in excess. The reactants may be present either in suspension or solution in the particular reaction medium. It is also possible in principle for the reactants to be reacted without a solvent, especially when the particular thioamide has a low melting point. The reaction is only slightly exothermic and may be carried out at between −10° C. and 150° C., preferably between 20° C. and 50° C. A temperature range between 0° C. and 40° C. usually proves to be particularly favorable.

The reaction time depends substantially on the reaction temperature and is between 2 minutes and 3 days at higher and lower temperatures respectively. In the favorable temperature range, the reaction time is generally between 5 minutes and 48 hours.

The compounds I'×HZ frequently separate out in the form of their acid addition salts of low solubility during the reaction, but it is expedient subsequently to add a suitable precipitant. Examples of ones which may be used are hydrocarbons such as benzene, toluene, cyclohexane or heptane or tetrachloromethane; in particular, alkyl acetates such as ethyl acetate or n-butyl acetate or dialkyl ethers such as diethyl ether, diisopropyl ether, di-n-butyl ether or tert-butyl methyl ether have proved to be particularly suitable. If the reaction mixture is still a solution after the end of the reaction, it is possible to precipitate the salts of the compounds I'×HZ, where appropriate after concentrating the reaction solution, with one of said precipitants. It is also possible and advantageous to filter the solution of the reaction mixture into a solution of one of said precipitants with stirring. Since the reaction of the compounds III with the thioureas IV takes place virtually quantitatively, the resulting crude products are usually already analytically pure. The reaction mixture may also be worked up by making the reaction mixture alkaline by adding an organic base such as, for example, triethylarnine or diisobutylamine or ammonia or morpholine or piperidine or 1,8-diazabicyclo [5.4.0]undec-7-ene, and purifying the crude reaction product after concentration by chromatography, for example on a silica gel column. Eluents which prove suitable for this are, for example, mixtures of ethyl acetate with methanol, mixtures of dichloromethane with methanol, mixtures of toluene with methanol or ethyl acetate or mixtures of ethyl acetate with hydrocarbons such as heptane. If the crude product is purified in the manner described last, it is possible to obtain from the pure base of the formula I' obtained in this way an acid addition product of the formula I'×H—B by dissolving or suspending the base in an organic protic solvent such as methanol, ethanol, propanol or isopropanol or in an organic aprotic solvent such as ethyl acetate, diethyl ether, diisopropyl ether, tert-butyl methyl ether, dioxane, tetrahydrofuran, acetone or butan-2-one, and then adding to this mixture an at least equimolar amount of an inorganic acid such as, for example, hydrochloric acid, dissolved in an inert solvent such as, for example, diethyl ether or ethanol, or another one of the inorganic or organic acids mentioned hereinbefore. The compounds of the formula I' may be recrystallized from a suitable inert solvent such as, for example, acetone, butan-2-one, acetonitrile, nitromethane. However, reprecipitation from a solvent such as, for example, dimethylformamide, dimethylacetamide, nitromethane, acetonitrile, preferably acetone or ethyl acetate, is particularly advantageous.

The reaction of the compounds of the formula III with the thioureas of the formula IV may also be carried out by adding an at least equimolar amount of a base such as, for example, triethylamine to the reaction mixture, and then converting the compounds I' obtained in this way where appropriate into their acid addition products I'×H—B.

Suitable as residue of an activated ester Z in the compounds of the formula III are, for example: Cl, Br, I, O—C(O)—($C_6H_4$)-4-$NO_2$, O—$SO_2$—$CH_3$, O—$SO_2$—$CF_3$, O-$SO_2$—($C_6H_4$)-4-$CH_3$, O—$SO_2$-$C_6H_5$.

The acid addition products I'×HZ and I × HZ may be converted into the compounds of the formula I' and I by treatment with bases. Examples of suitable bases are solutions of inorganic hydroxides such as lithium, sodium, potassium, calcium or barium hydroxide, carbonates or bicarbonates, such as sodium or potassium carbonate, sodium or potassium bicarbonate, ammonia and amines such as triethylamine, diisopropylamine, dicyclohexylamine, piperidine, morpholine, methyldicyclohexylamine.

Thioureas of the formula IV either are commercially available or may be prepared by methods known from the literature.

The compounds of the formula I × HZ or I where R2 is ($C_1$–$C_6$)-alkyl, ($C_3$–$C_6$)-cycloalkyl, $(CH_2)_n$-phenyl, $(CH_2)_n$-thienyl, $(CH_2)_n$-pyridyl, $(CH_2)_n$-furyl, and where n is 0–5 may be obtained by either aa) reacting the acid addition salts of the formula I'×HZ in a solvent of the formula R2—OH, where R2 has the meaning described above, at a temperature of from −20° C. to 100° C., preferably at −5° C. to 50° C., for from 2 hours to 4 days, preferably 4 hours to 2 days, or ab) reacting the free bases of the formula I' in a solvent of the formula R2—OH, where R2 has the meaning described above, with equimolar, less than stoichiometric or catalytic, preferably catalytic, amounts of an inorganic or organic acid as described hereinbefore, or with addition of an acid ionic exchanger at a temperature of from −20° C. to 100° C., preferably at −5° C. to 50° C., for from 2 hours to 4 days, preferably 4 hours to 2 days, or ac) carrying out the reactions according to aa) and ab) in an inert aprotic solvent such as dichloromethane, chloroform, 1,2-dichloroethane, heptane, benzene, toluene, acetonitrile, nitromethane, dioxane, tetrahydrofuran, ethylene glycol dimethyl ether, diethyl ether, diisopropyl ether, tert-butyl methyl ether, acetone, butan-2-one or a lower alkyl acetate such as, for example, ethyl acetate, by adding from 1 to 5, preferably 1.5–2, equivalents of a compound of the formula R2—OH, or ad) converting compounds of the formula I' in a polar aprotic solvent such as, for example, tetrahydrofuran, dioxane, ethylene glycol dimethyl ether, nitromethane, acetonitrile or dimethylformamide, dimethylacetamide or N-methyl-2-pyrrolidone, with the aid of a base such as, for example, sodium hydride, lithium diisopropylamide, KOH or potassium carbonate, into their alcoholate, and then reacting the latter with addition of an alkylating agent of the formula R2—W where W=chlorine, bromine, iodine, O—C(O)—$CH_3$, O-C(O)—$CF_3$, O—C(O)—$C_6H_4$-4-$NO_2$, O—$SO_2$—$CH_3$, O—$SO_2$—$CF_3$, O—$SO_2$—$C_6H_4$-4-$CH_3$, O—$SO_2$—$C_6H_4$-4—$NO_2$, at −20 to 150° C., preferably at −15 to 50° C., for from 10 minutes to 2 days, preferably for 20 minutes to 12 hours. Compounds of the formula I × HZ or I with R2=C(O)—($C_1$–$C_6$)-alkyl, C(O)—($C_3$–$C_6$)-cycloalkyl, C(O)—$(CH_2)_n$-phenyl, C(O)—$(CH_2)_n$-thienyl, C(O)—$(CH_2)_n$-pyridyl, C(O)—$(CH_2)_n$-furyl, where n is 0–5, may be obtained by either:

ba) proceeding as described under aa)–ac) with the difference that an acid R2—OH is employed in place of an alcohol R2—OH, and from 1 to 2 equivalents of the acid R2—OH, preferably 1.5 equivalents of the acid R2—OH, are employed, and the inorganic or organic acid catalyst described in aa)–ac) is not added but the acid cation exchanger is advantageously employed or bb) reacting a compound of the formula I' with an acid of the formula R2—OH in a Mitsunobu Reaction (O. Mitsunobu, Synthesis 1981, 1) to give a compound of the formula I or bc) reacting a carbonyl chloride of the formula R2—Cl or a carboxylic anhydride of the formula R2—O—R2 with a compound of the formula I' in an alcohol esterification (Houben-Weyl, Methoden der Organischen Chemie, Georg Thieme Verlag Stuttgart, Volume E5, pp. 656–715).

The examples detailed below serve to illustrate the invention without, however, restricting it. The measured melting or decomposition points (m.p.) have not been corrected and generally depend on the heating rate.

TABLE 1

Examples

Formula I

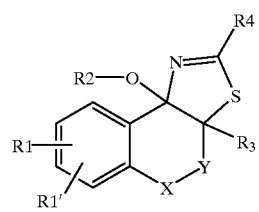

| Example | R1; R1' | R2 | R3 | R4 | Y | X | Salt | m.p. [° C.] |
|---|---|---|---|---|---|---|---|---|
| A01 | 5-$NO_2$ | H | H | $NH_2$ | — | $CH_2$ | — | >260 |
| A02 | 5-$NO_2$ | H | H | $NH(CH_3)$ | — | $CH_2$ | — | >260 |

TABLE 1-continued

Examples

Formula I

| Example | R1; R1' | R2 | R3 | R4 | Y | X | Salt | m.p. [° C.] |
|---|---|---|---|---|---|---|---|---|
| A03 | 6-Cl | H | H | NH$_2$ | — | CH$_2$ | HCl | 241 |
| A04 | 6-Cl | H | H | NH(CH$_3$) | — | CH$_2$ | HCl | 249 |
| A05 | 5-SO$_2$CH$_3$ | H | H | NH$_2$ | — | CH$_2$ | — | >230 |
| A06 | 5-SO$_2$CH$_3$ | H | H | NH(CH$_3$) | — | CH$_2$ | — | >230 |
| A07 | 5-SO$_2$CH$_3$; 6-Cl | H | H | NH(C$_6$H$_5$) | — | CH$_2$ | — | 130 |
| A08 | 7-Cl | H | H | NH(CH$_3$) | — | CH$_2$ | — | 180 |
| A09 | 5-Cl | H | H | NH(CH$_3$) | — | CH$_2$ | — | 207 |
| A10 | 6-F | H | H | NH(CH$_3$) | — | CH$_2$ | — | 206 |
| A12 | 6-C$_6$H$_5$ | H | H | NH(CH$_3$) | — | CH$_2$ | HBr | 265 |
| A13 | 6-(C$_6$H$_4$-3-CF$_3$) | H | H | NH(CH$_3$) | — | CH$_2$ | HBr | 199 |
| A14 | 6-CN | H | H | NH(CH$_3$) | — | CH$_2$ | HBr | 287 |
| A15 | 6-(thien-3-yl) | H | H | NH(CH$_3$) | — | CH$_2$ | HBr | 180 |
| A16 | 6-(C$_6$H$_4$-3-F) | H | H | NH(CH$_3$) | — | CH$_2$ | HBr | 228 |
| A17 | 6-Cl | H | H | NH$_2$ | — | CH$_2$ | HBr | 292 |
| A18 | 6-(C$_6$H$_4$-4-CH$_3$) | H | H | NH(CH$_3$) | — | CH$_2$ | HBr | 196 |
| A19 | 6-Cl | H | H | NH$_2$ | — | CH$_2$ | HCl | 251 |
| A20 | 6-(C$_6$H$_4$-4-CF$_3$) | H | H | NH(CH$_3$) | — | CH$_2$ | HBr | 195 |
| A21 | 6-(C$_6$H$_3$-3,5-di-CF$_3$) | H | H | NH(CH$_3$) |  | CH$_2$ | HBr | 266 |
| A22 | 6-(C$_6$H$_4$-3-Cl) | H | H | NH(CH$_3$) | — | CH$_2$ | HBr | 203 |
| A23 | 6-(C$_6$H$_4$-3-OCF$_3$) | H | H | NH(CH$_3$) | — | CH$_2$ | HBr | 236 |
| A24 | 6-(C$_6$H$_4$-4-Cl) | H | H | NH(CH$_3$) | — | CH$_2$ | HBr | 186 |
| A25 | 5-C(CH$_3$)$_3$ | H | H | NH(CH$_3$) | — | CH$_2$ | HBr | 273 |
| A26 | 6-(C$_6$H$_4$-2-CF$_3$) | H | H | NH(CH$_3$) | — | CH$_2$ | HBr | 196 |
| A27 | 6-(C$_6$H$_4$-3-OCH$_3$) | H | H | NH(CH$_3$) | — | CH$_2$ | HBr | 195 |
| A28 | 6-(naphth-1-yl) | H | H | NH(CH$_3$) | — | CH$_2$ | HBr | 211 |
| A29 | 7-(C$_6$H$_4$-4-CF$_3$) | H | H | NH(CH$_3$) | — | CH$_2$ | HBr | 191 |
| A30 | 7-(C$_6$H$_4$-4-CF$_3$) | H | H | NH$_2$ | — | CH$_2$ | HBr | 230 |
| A31 | 5-(C$_6$H$_4$-4-Cl) | H | H | N(CH$_3$)$_2$ | — | CH$_2$ | HBr | 223 |
| A32 | 5-(C$_6$H$_4$-4-CF$_3$) | H | H | NH$_2$ | — | CH$_2$ | HBr | 229 |
| A33 | 6-OCF$_3$ | H | H | NH(CH$_3$) | — | CH$_2$ | HBr | 267 |
| A34 | 5-C(CH$_3$)$_3$ | H | H | NH$_2$ | — | CH$_2$ | HBr | 272 |
| A35 | 6-OCF$_3$ | H | H | NH$_2$ | — | CH$_2$ | HBr | 253 |
| A36 | 6-Cl | H | H | NH—N=C(CH$_3$)$_2$ | — | CH$_2$ | HBr | 237 |
| A37 | 6-Cl | H | H | NH—NH$_2$ | — | CH$_2$ | HBr | 146 |
| A38 | 6-Cl | H | CH$_3$ | NH$_2$ | — | CH$_2$ | HBr | 229 |
| A39 | 6-O-CH$_2$—CF$_2$—CF$_2$—CF$_3$ | H | H | NH(CH$_3$) | — | CH$_2$ | HCl | 239 |
| A40 | 6-Cl | H | H | NH$_2$ | — | CH$_2$ | — | 87 |
| A41 | 6-CCH | H | H | NH$_2$ | — | CH$_2$ | HBr | >300 |
| A42 | 6-O-(C$_6$H$_4$-4-Cl) | H | H | NH$_2$ | — | CH$_2$ | HBr | 227 |
| A43 | 6-Cl | H | F | NH$_2$ | — | CH$_2$ | — | 159 |
| A44 | 6-Cl | H | F | NH—CH$_3$ | — | CH$_2$ | — | 182 |
| A45 | H | H | F | NH$_2$ | — | CH$_2$ | — | 160 |
| A46 | H | H | F | NH—CH$_3$ | — | CH$_2$ | — | 165 |
| A47 (−) | 6-Cl | H | F | NH—CH$_3$ | — | CH$_2$ | — | Decomp. from 105 |
| A48 (+) | 6-Cl | H | F | NH—CH$_3$ | — | CH$_2$ | — | Decomp. from 105 |
| A49 (−) | 6-Cl | H | F | NH—CH$_3$ | — | CH$_2$ | HCl | 163 |
| A50 (+) | 6-Cl | H | F | NH—CH$_3$ | — | CH$_2$ | HCl | 163 |
| A51 | 6-Cl | H | F | NH$_2$ | — | CH$_2$ | HCl | Decomp. from 225 |

The compounds of the formula I are distinguished by beneficial effects on lipid metabolism, and they are particularly suitable as anorectic agents. The compounds may be employed alone or in combination with other anorectic active ingredients. Further anorectic active ingredients of this type are mentioned, for example, in the Rote Liste, chapter 01 under weight-reducing agents/appetite suppressants. Examples include, but are not limited to, Decorpa© (from Pierre Fabre Pharma, common name, sterculia), Xenical©) (from Roche, common name, orlistat), Antiadipositum X-112S (from Haenseler, common name, D-norpseudoephedrin-HCl), Fasupond© (from Eu Rho Arzneil, common name, D-norpseudoephedrin-HCl), Mirapront© N (from Mack, Illert., common name, D-norpseudoephedrin-Poly(styrol, divinylbenzol) sulfonate), Regenon©) l-retard (from Temmler Pharma, common name, Amfepramon-HCl), Rondimen©) (from ASTA Medica AWD, common name, Mefenorex-HCl), Tenuate© Retard (from Artegodan, common name, Amfepramon-HCl), Vita-Schlanktropfen Schuck (from Schuck, common name, D-norpseudoephedrin-HCl), Vencipon© N (from Artesan, common name, Ephedrin-HCl), Cefamadar© (from Cefak, common name Madar D4), and Helianthus tuberosus (Plantina). The compounds are suitable for the treatment of obesity. The compounds are furthermore suitable for the treatment of type II diabetes.

The activity of the compounds has been tested as follows:
Biological test model:
The anorectic effect was tested on male NMRI mice. After withdrawal of feed for 24 hours, the test product was administered by gavage. The animals were housed singly and had free access to drinking water and, 30 minutes after administration of the product, they were offered condensed milk. The consumption of condensed milk was determined, and the general behavior of the animals was inspected, every half hour for 7 hours. The measured milk consumption was compared with that of untreated control animals.

vent is removed from the organic phase in vacuo. The residue is purified by column filtration (silica gel; dichloromethane). 2-Bromo-6-nitroindan-1-one is obtained with a melting point of 113° C.

b) 2-Amino-5-nitro-8,8a-dihydroindeno[1,2-d]thiazol-3a-ol:

1.28 g (5 mmol) of 2-bromo-6-nitroindan-1-one are dissolved in 30 ml of acetone and, while stirring, 530 mg of thiourea in 10 ml of acetone are added. The solution is initially clear but, after a few minutes, the hydrobromide of 2-amino-5-nitro-8,8a-dihydroindeno[1,2-d]thiazol-3a-ol crystallizes out. It is stirred at room temperature for 1 h, filtered off with suction and washed with a little acetone. The air-dried hydrobromide is dissolved in about 10 ml of methanol and, after addition of 0.7 ml of triethylamine, stirred for 15 min. Then 50 ml of water are added, and the mixture is stirred at room temperature for 1 h. The crystals which have formed are filtered off with suction and washed with a little cold water. 2-Amino-5-nitro-8,8a-dihydroindeno[1,2-d]thiazol-3a-ol is obtained with a melting point above 250° C.

TABLE 2

Anorectic effect measured by reduction in the cumulative milk consumption by treated animals compared with untreated animals.

Compound/Example Formula I

| | Oral dose [mg/kg] | Number of animals/ cumulative milk consumption by the treated animals N/[ml] | Number of animals/ cumulative milk consumption by the untreated control animals N/[ml] | Reduction in the cumulative milk consumption as % of the controls |
|---|---|---|---|---|
| Example A04 | 50 | 8/0.56 | 8/3.18 | 82 |
| Example A14 | 50 | 12/0.68 | 12/3.87 | 82 |
| Example A19 | 50 | 5/0.28 | 5/4.00 | 93 |
| Example A31 | 50 | 5/0.42 | 5/4.18 | 90 |
| Example A32 | 50 | 5/0.80 | 5/5.42 | 85 |
| Example A33 | 50 | 5/0.80 | 5/3.12 | 74 |
| Example A34 | 50 | 5/0.54 | 5/3.12 | 83 |
| Example A36 | 50 | 5/1.54 | 5/5.06 | 70 |
| Example A39 | 50 | 5/0.58 | 5/3.58 | 84 |
| Example A40 | 50 | 5/0.18 | 5/3.52 | 95 |
| Example A44 | 50 | 5/0.32 | 5/3.40 | 91 |
| Example A46 | 50 | 5/0.88 | 5/4.52 | 81 |
| Example A49 | 10 | 5/0.44 | 5/3.72 | 88 |
| Example A50 | 10 | 5/0.22 | 5/4.02 | 94 |
| Example A51 | 10 | 5/0.84 | 5/3.80 | 78 |

The above data shows that the compounds of the formula I exhibit a very good anoretic effect.

The preparation of some examples is described in detail below, and the other compounds of the formula I were obtained analogously:

Procedure Example 1:
2-Amino-5-nitro-8,8a-dihydroindeno[1,2-d]thiazol-3a-ol (compound of Example 1):
a) 2-Bromo-6-nitroindan-1-one:

7.1 g (0.04 mol) of 5-nitroindan-1-one are dissolved in 135 ml of glacial acetic acid, and 1.12 ml of 48 percent hydrobromic acid solution are added. Then 2.06 ml of bromine in 40 ml of glacial acetic acid are added dropwise at room temperature to the solution, which is then stirred for 2 h. The reaction mixture is poured into ice-water and extracted with dichloromethane and, after drying, the sol- Procedure Example 2:
3a-Hydroxy-2-methylamino-8,8a-dihydro-3aH-indeno[1,2-d]thiazole-6-carbonitrile hydrobromide (compound of Example 14):
a) 1-Oxoindane-5-carbonitrile:

9.5 g of 5-bromo-1-indanone and 4.93 g of CuCN are suspended in 10 ml of dimethylformamide and boiled under reflux for 4 hours. A solution of 18 g of iron(III) chloride in 5 ml of concentrated hydrochloric acid with 30 ml of water are added dropwise to the cooled, dark-brown viscous suspension while stirring, and the mixture is then stirred at 70° C. for 30 minutes. The reaction mixture is extracted by shaking three times with 50 ml of toluene, and the combined organic phases are extracted by shaking with 50 ml of 2N hydrochloric acid and 50 ml of 2N sodium hydroxide solution and then washed with water until neutral. The toluene extract is dried over magnesium sulfate and concentrated in vacuo, and the residue is recrystallized from n-heptane. 1-oxoindane-5-carbonitrile is obtained with a melting point of 123–125° C.

b) 2-Bromo-1-oxoindane-5-carbonitrile:

3.93 g of 1-oxoindane-5-carbonitrile are dissolved in 40 ml of glacial acetic acid and, after addition of 0.1 ml of hydrobromic acid (48% strength in water), at room temperature a solution of 1.34 ml of bromine in 8 ml of acetic acid is added dropwise. The reaction mixture is stirred at room temperature for 3 h and then added to a mixture of 20 g of ice and 40 g of water, 0.5 g of sodium bisulfite is added and the mixture is extracted by shaking twice with 50 ml of dichloromethane each time. The organic phase is washed with 50 ml of water, dried over magnesium sulfate, concentrated in vacuo and chromatographed on silica gel with toluene/ethyl acetate 25/1. 2-Bromo-l-oxoindane-5-carbonitrile is obtained with a melting point of 115–118° C.

c) 3a-Hydroxy-2-methylamino-8,8a-dihydro-3aH-indeno[1,2-d]thiazole-6-carbonitrile hydrobromide:

236 mg of 2-bromo-1-oxoindane-5-carbonitrile are dissolved in 10 ml of acetone and, at 0° C., 135 mg of N-methylthiourea are added. The mixture is stirred at room temperature for 3 h and at ice-bath temperature for 90 minutes. The precipitate is filtered off with suction, washed with acetone and dried in vacuo. The hydrobromide of 3a-hydroxy-2-methylamino-8,8a-dihydro-3aH-indeno[1,2-d]thiazole-6-carbonitrile is obtained with a melting point of 287–288° C.

Procedure Example 3:
2-Amino-5-(4-trifluoromethylphenyl)-8,8a-dihydroindeno[1,2-d]thiazol-3a-ol hydrobromide (compound of Example 32):

a) 6-(4-Trifluoromethylphenyl)indan-1-one):

6.33 g of 6-bromoindan-1-one are suspended with 5.7 g of 4-trifluoromethylbenzeneboronic acid and 6.36 g of sodium carbonate in a mixture of 100 ml of dry toluene with 20 ml of dry ethanol and 20 ml of water and, after addition of 338 mg of palladium(II) acetate and 787 mg of triphenylphosphine, refluxed under argon for 4 h. The reaction mixture is cooled, the ethanol content is removed in vacuo, and the residue is stirred with 40 ml of 0.5 N sodium hydroxide solution for 10 minutes and filtered off with suction through a clarifying layer. The resulting solution is washed three times with 50 ml of water and once with 50 ml of saturated brine, dried over magnesium sulfate, concentrated in vacuo and chromatographed on silica gel with dichloromethane/heptane 3/1.6-(4-Trifluoromethylphenyl)indan-1-one is obtained and is employed without further purification in the next stage.

b) 2-Bromo-6-(4-trifluoromethylphenyl)indan-1-one:

The bromination is carried out as described in Procedure Example 2b and affords 2-bromo-6-(4-trifluoromethylphenyl)indan-1-one with a melting point of 105° C.

c) 2-Amino-5-(4-trifluoromethylphenyl)-8,8a-dihydroindeno[1,2-d]thiazol-3a-ol hydrobromide:

1.06 g of 2-bromo-6-(4-trifluoromethylphenyl)indan-1-one are dissolved with 266 mg of thiourea in 10 ml of dry acetone and stirred at ice-bath temperature for 4 h. The precipitate is filtered off with suction, washed with acetone and dried in vacuo. The hydrobromide of 2-amino-5-(4-trifluoromethylphenyl)-8,8a-dihydroindeno[1,2-d]thiazol-3a-ol is obtained with a melting point of 228–230° C.

Procedure Example 4:
2-Amino-6-chloro-8a-methyl-8,8a-dihydroindeno[1,2-d]thiazol-3a-ol hydrobromide (compound of Example 38):

20 g of 5-chloroindan-1-one are dissolved in 600 ml of dry toluene and, after addition of 27.4 ml of N,N-dimethylhydrazine and 1 g of p-toluenesulfonic acid, boiled with a water trap for 4 h. The reaction mixture is concentrated in vacuo, and the residue is dissolved in ethyl acetate and washed with sodium bicarbonate solution and then with water. The organic phase is dried over sodium sulfate and concentrated in vacuo, and the residue is chromatographed on silica gel with ethyl acetate/heptane ½. N'-(5-chloroindan-1-ylidene)-N,N-dimethylhydrazine is obtained as an oil.

33.1 ml of a 2M solution of lithium diisopropylamide in THF/heptane/ethylbenzene are added dropwise to 300 ml of dry tetrahydrofuran (THF) under argon. At −70° C., 12 g of N'-(5-chloroindan-1-ylidene)-N,N-dimethylhydrazine, dissolved in 100 ml of dry THF, are added dropwise to this solution. After the reaction mixture has been stirred at −70° C. for 1 h and at −40° C. for a further 3 h, 3.882 ml of methyl iodide are added dropwise and the mixture is stirred further overnight. 200 ml of water are added dropwise to the reaction mixture which has warmed to room temperature; the THF is removed in vacuo, and the residue is extracted with ethyl acetate. The ethyl acetate extract is treated with active carbon, dried over sodium sulfate, filtered, concentrated in vacuo and chromatographed on silica gel with ethyl acetate/heptane ½. N'-(5-chloro-2-methylindan-1-ylidene)-N,N-dimethylhydrazine is obtained as an oil.

5.5 g of N'-(5-chloro-2-methylindan-1-ylidene)-N,N-dimethylhydrazine are emulsified in 100 ml of 2N sulfuric acid and boiled under reflux for 4 h. The cooled reaction mixture is cautiously extracted with ethyl acetate; the organic extract is extracted several times with saturated sodium bicarbonate solution, dried over sodium sulfate, filtered, dried in vacuo and chromatographed on silica gel with ethyl acetate/hetpane ⅕. 5-Chloro-2-methylindan-1-one is obtained as an oil.

Bromination of 5-chloro-2-methylindan-1-one is carried out as described in Procedure Example 2b) and affords 2-bromo-5-chloro-2-methylindan-1-one as an oil, which is employed without further purification in the next stage.

1.5 g of 2-bromo-5-chloro-2-methylindan-1-one are dissolved together with 460 mg of thiourea in 50 ml of triacetone and boiled under reflux for 8 h. The precipitate is filtered off with suction, washed with acetone and dried in vacuo. 2-Amino-6-chloro-8a-methyl-8,8a-dihydroindeno[1,2-d]thiazol-3a-ol hydrobromide is obtained and melts at 229° C. with decomposition.

Procedure Example 5:
6-(2,2,3,3,4,4,4-Heptafluorobutoxy)-2-methylamino-8,8a-dihydroindeno[1,2-d]thiazol-3a-ol hydrochloride (compound of Example 39):

a) 6-(2,2,3,3,4,4,4-Heptafluorobutoxy)-2-methylamino-8,8a-dihydroindeno[1,2-d]thiazol-3a-ol hydrobromide is obtained by reacting 1.7 g of 2-bromo-5-(2,2,3,3,4,4,4-heptafluorobutoxy)indan-1-one with 0.31 g of N-methylthiourea in 30 ml of ethyl acetate and stirring at room temperature for 24 hours as colorless crystalline precipitate. Melting point 280–282° C. (decomposition)

b) 6-(2,2,3,3,4,4,4-Heptafluorobutoxy)-2-methylamino-8,8a-dihydroindeno[1,2-d]thiazol-3a-ol is obtained by treating 0.9 g of 6-(2,2,3,3,4,4,4-heptafluorobutoxy)-2-methylamino-8,8a-dihydroindeno[1,2-d]thiazol-3a-ol hydrobromide with 0.72 g of triethylamine in 30 ml of ethanol. After leaving to stand overnight, the crystalline precipitate is filtered off and washed several times with water. Colorless crystals, melting point 178–180° C.

c) 6-(2,2,3,3,4,4,4-Heptafluorobutoxy)-2-methylamino-8,8a-dihydroindeno[1,2-d]thiazol-3a-ol hydrochloride is obtained by adding an ethereal solution of gaseous hydrogen chloride to a solution of 0.6 g of 6-(2,2,3,3,4,4,4-heptafluorobutoxy)-2-methylamino-8,8a-dihydroindeno[1,2-d]thiazol-3a-ol in 20 ml of ethyl acetate. The mixture is stirred at room temperature for about 1 day, and the colorless crystalline precipitate is filtered off. Melting point 238–240° C.

Procedure Example 6:
2-Amino-6-chloro-8a-fluoro-8,8a-dihydroindeno[1,2-d]thiazol-3a-ol (compound of Example 43):
a) 5-Chloro-2-fluoroindan-1-one:

25 ml of a 1.6 molar solution of n-butyllithium in n-hexane are slowly added dropwise to a solution of 5.24 ml of diisopropylamine in 60 ml of dry tetrahydrofuran at a temperature of<–50° C.; the mixture is then stirred at –50° C. for a further 10 minutes. A solution of 6.33 g of 5-chloroindan-1-one in 60 ml of dry tetrahydrofuran is then slowly added, and the mixture is stirred at –50° C. for a further 20 minutes. Finally, 11.4 g of diphenyl-N-fluorosulfimide, dissolved in 60 ml of dry tetrahydrofuran, are added dropwise. The mixture is allowed to warm to 0° C. with stirring over the course of 2 hours, 120 ml of saturated sodium bicarbonate solution are added dropwise, the tetrahydrofuran is distilled out in vacuo, and the residue is extracted by shaking twice with 150 ml of ethyl acetate. The organic phase is washed with water and saturated brine, dried over magnesium sulfate, concentrated and purified by chromatography on silica gel with diisopropyl ether/n-heptane 1/1. 5-Chloro-2,2-difluoroindan-1-one is obtained with a melting point of 102–104° C. in addition to 5-chloro-2-fluoroindan-1-one.

b) 5-Chlor-2-bromo-2-fluoroindan-1-one:

Bromination of 5-chloro-2-fluoroindan-1-one takes place as described in Procedure Example 2b) and affords 5-chloro-2-bromo-2-fluoroindan-1-one with a melting point of 104–105° C.

2-Amino-6-chloro-8a-fluoro-8,8a-dihydroindeno[1,2-d]thiazol-3a-ol:

263 mg of 5-chloro-2-bromo-2-fluoroindan-1-one and 152 mg of thiourea are dissolved in 2.5 ml of dry dimethyl sulfoxide and stirred at 50° C. for 8 h. Excess triethylamine is added to the reaction mixture, which is then concentrated in vacuo. The residue is purified by chromatography on silica gel with ethyl acetate as eluent. 2-Amino-6-chloro-8a-fluoro-8,8a-dihydroindeno[1,2-d]thiazol-3a-ol is obtained with a melting point of 159° C.

Inventors hereby incorporate by reference the prior application DE 19908539.0 filed Feb. 26, 1999.

What is claimed is:

1. A compound of the formula I

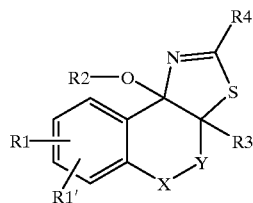

I in which

Y is a direct linkage, —CH$_2$— or —CH$_2$—CH$_2$—;

X is CH$_2$, CH(CH$_3$), CH(C$_2$H$_5$), CH(C$_3$H$_7$) or CH(C$_6$H$_5$);

R1, R1' are independently H, F, Cl, Br, I, CF$_3$, NO$_2$, CN, COOH, COO(C$_1$–C$_6$)alkyl, CONH$_2$, CONH(C$_1$–C$_6$) alkyl, CON[(C$_1$–C$_6$)alkyl]$_2$, (C$_1$–C$_6$)-alkyl, (C$_2$–C$_6$)-alkenyl, (C$_2$–C$_6$)-alkynyl, O—(C$_1$–C$_6$)-alkyl (where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$—(CH$_2$)$_n$-phenyl (where n is 0–6 and the phenyl radical may be substituted up to two times by F, Cl, Br, OH, CF$_3$, NO$_2$, CN, OCF$_3$, O—(C$_1$–C$_6$)-alkyl, (C$_1$–C$_6$)-alkyl or NH$_2$), NH$_2$, NH—(C$_1$–C$_6$)-alkyl, N((C$_1$–C$_6$)-alkyl)$_2$, NH(C$_1$–C$_7$)-acyl, phenyl, biphenylyl, O—(CH$_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted up to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position 1 or 2 by methyl or benzyl);

R2 is H, (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, (CH$_2$)$_n$-furyl, C(O)—(C$_1$–C$_6$)-alkyl, C(O)—(C$_3$–C$_6$)-cycloalkyl, C(O)—(CH$_2$)$_n$-phenyl, C(O)—(CH$_2$)$_n$-thienyl, C(O)—(CH$_2$)$_n$-pyridyl or C(O)—(CH$_2$)$_n$-furyl (where n is 0–5 and wherein phenyl, thienyl, pyridyl, furyl may each be substituted up to two times by Cl, F, CN, CF$_3$, (C$_1$–C$_3$)-alkyl, OH or O—(C$_1$–C$_6$)-alkyl);

R3 is H, (C$_1$–C$_6$)-alkyl, F, CN, N$_3$, O—(C$_1$–C$_6$)-alkyl, (CH$_2$)$_n$-phenyl, (CH$_2$)$_n$-thienyl, (CH$_2$)$_n$-pyridyl, (CH$_2$)$_n$-furyl (where n is 0–5 and wherein phenyl, thienyl, pyridyl, furyl may each be substituted up to two times by Cl, F, CN, CF$_3$, (C$_1$–C$_3$)-alkyl, OH or O—(C$_1$–C$_6$)-alkyl), (C$_2$–C$_6$)-alkynyl, (C$_2$–C$_6$)-alkenyl, C(O)OCH$_3$, C(O)OCH$_2$CH$_3$, C(O)OH, C(O)NH$_2$, C(O)NHCH$_3$, C(O)N(CH$_3$)$_2$ or OC(O)CH$_3$;

R4 is NR6R7;

R6 and R7 are independently H, (C$_1$–C$_6$)-alkyl, (C$_3$–C$_6$)-cycloalkyl, phenyl (wherein the phenyl ring may be optionally substituted up to two times by Cl, F, CN, CF$_3$, (C$_1$–C$_3$)-alkyl, OH or O—(C$_1$–C$_6$)-alkyl), CO—(C$_1$–C$_6$)-alkyl, CHO, CO—phenyl, —NH$_2$, —N═C (CH$_3$)$_2$, -(pyrrolidin-1-yl), -(piperidin-1-yl), -(morpholin-4-yl), -(piperazin-1-yl) or -(4-methylpiperazin-1-yl), or NR6R7 is a ring selected from the group consisting of pyrrolidine, piperidine, morpholine, piperazine, 4-methylpiperazin-1-yl, 4-benzylpiperazin-1-yl and phthalimidyl;

and its physiologically tolerated salts and physiologically functional derivatives.

2. A compound of the formula I as claimed in claim 1, wherein

Y a direct linkage;

X CH$_2$;

R1, R1' are independently H, F, Cl, CF$_3$, NO$_2$, CN, COOH, COO(C$_1$–C$_6$)alkyl, CONH$_2$, CONH(C$_1$–C$_6$) alkyl, CON[(C$_1$–C$_6$)alkyl]$_2$, (C$_1$–C$_6$)-alkyl, (C$_2$–C$_6$)-alkenyl, (C$_2$–C$_6$)-alkynyl, O—(C$_1$–C$_6$)-alkyl (where one, more than one or all hydrogen(s) in the alkyl radicals may be replaced by fluorine or one hydrogen may be replaced by OH, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$NH(C$_1$–C$_6$)-alkyl, SO$_2$N[(C$_1$–C$_6$)-alkyl]$_2$, SO$_2$—(C$_1$–C$_6$)-alkyl, SO$_2$—(CH$_2$)$_n$-phenyl (where n is 0–6 and the phenyl radical may be substituted by F, Cl, Br, OH, CF$_3$, NO$_2$, CN, OCF$_3$, O—(C$_1$–C$_6$)-alkyl, (C$_1$–C$_6$)-alkyl or NH$_2$), NH$_2$, NH—(C$_1$–C$_6$)-alkyl, N((C$_1$–C$_6$)-alkyl)$_2$, NH(C$_1$–C$_7$)-acyl, phenyl, biphenylyl, O—(CH$_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings each may be optionally substituted once or twice by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R2 is H, (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, (CH$_2$)$_n$-furyl, C(O)—(C$_1$–C$_6$)-alkyl, C(O)—(C$_3$–C$_6$)-cycloalkyl, C(O)—(CH$_2$)$_n$-phenyl, C(O)—(CH$_2$)$_n$-thienyl, C(O)—(CH$_2$)$_n$-pyridyl or C(O)—(CH$_2$)$_n$-furyl (where n is 0–5 and wherein phenyl, thienyl, pyridyl, furyl may each be substituted up to two times by Cl, F, CN, CF$_3$, (C$_1$–C$_3$)-alkyl, OH or O—(C$_1$–C$_6$)-alkyl), R3 is H, (C$_1$–C$_6$)-alkyl, F, (CH$_2$)$_n$-phenyl, (CH$_2$)$_n$-thienyl, (CH$_2$)$_n$-pyridyl, (CH$_2$)$_n$-furyl (where n is 0–5 and in which phenyl, thienyl, pyridyl, furyl may each be substituted up to two times by Cl, F, CN, CF$_3$, (C$_1$–C$_3$)-alkyl, OH or O—(C$_1$–C$_6$)-alkyl), (C$_2$–C$_6$)-alkynyl, (C$_2$–C$_6$)-alkenyl, C(O)OCH$_3$, C(O)OCH$_2$CH$_3$, C(O)OH, C(O)NH$_2$, C(O)NHCH$_3$, C(O)N(CH$_3$)$_2$ or OC(O)CH$_3$;

R4 is NR6R7;

R6 and R7 are independently H, (C$_1$–C$_6$)-alkyl, (C$_3$–C$_6$)-cycloalkyl, phenyl (wherein the phenyl ring may be optionally substituted up to two times by Cl, F, CN, CF$_3$, (C$_1$–C$_3$)-alkyl, OH or O—(C$_1$–C$_6$)-alkyl), CO—(C$_1$–C$_6$)-alkyl, CHO, CO-phenyl, —NH$_2$, —N=C(CH$_3$)$_2$, -(pyrrolidin-1-yl), -(piperidin-1-yl), -(morpholin-4-yl), -(piperazin-1-yl) or -(4-methylpiperazin-1-yl), or NR6R7 is a ring selected from the group consisting of pyrrolidine, piperidine, morpholine, piperazine, 4-methylpiperazin-1-yl, 4-benzylpiperazin-1-yl and phthalimidyl;

and its physiologically tolerated salts and physiologically functional derivatives.

3. A compound of the formula I as claimed in claim 1, wherein

Y a direct linkage;

X CH$_2$;

R1, R1' are independently H, F, Cl, CF$_3$, CN, COOH, COO(C$_1$–C$_6$)alkyl, CONH$_2$, CONH(C$_1$–C$_6$)alkyl, CON[(C$_1$–C$_6$)alkyl]$_2$, (C$_1$–C$_6$)-alkyl, (C$_2$–C$_6$)-alkenyl, (C$_2$–C$_6$)-alkynyl, O—(C$_1$–C$_6$)-alkyl (where one, more than one or all hydrogen(s) in the alkyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$), SO$_2$—(C$_1$–C$_6$)-alkyl, SO$_2$—(CH$_2$)$_n$-phenyl (where n is 0–3 and the phenyl radical may be substituted by F, Cl, OH, CF$_3$, CN, OCF$_3$, O—(C$_1$–C$_6$)-alkyl, (C$_1$–C$_6$)-alkyl or NH$_2$), NH$_2$, NH—(C$_1$–C$_6$)-alkyl, N((C$_1$–C$_6$)-alkyl)$_2$, NH(C$_1$–C$_7$)-acyl, phenyl, biphenylyl, O—(CH$_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl, thienyl rings may be optionally substituted once or twice by F, Cl, OH, CF$_3$, CN, OCF$_3$, O—(C$_1$–C$_4$)-alkyl, (C$_1$–C$_4$)-alkyl, NH$_2$, NH(C$_1$–C$_4$)-alkyl, N((C$_1$–C$_4$)-alkyl)$_2$, SO$_2$—CH$_3$, COOH, COO—(C$_1$–C$_4$)-alkyl or CONH$_2$), 1,2,3-triazol-5-yl (wherein the triazole ring may be optionally substituted in position 1, 2 or 3 by methyl or benzyl) or tetrazol-5-yl (wherein the tetrazole ring may be optionally substituted in position 1 or 2 by methyl or benzyl);

R2 is H, (C$_1$–C$_6$)-alkyl, (CH$_2$)$_n$-phenyl, (CH$_2$)$_n$-thienyl, (CH$_2$)$_n$-pyridyl, (CH$_2$)$_n$-furyl (wherein phenyl, thienyl, pyridyl, furyl may each be substituted up to two times by Cl, F, CN, CF$_3$, (C$_1$–C$_3$)-alkyl, OH or O—(C$_1$–C$_6$)-alkyl);

R3 is H, F or (C$_1$–C$_4$)-alkyl;

R4 is NR6R7;

R6 and R7 are independently H, (C$_1$–C$_6$)-alkyl, (C$_3$–C$_6$)-Cycloalkyl, phenyl (wherein the phenyl ring may be optionally substituted up to two times by Cl, F, CN, CF$_3$, (C$_1$–C$_3$)-alkyl, OH or O—(C$_1$–C$_6$)-alkyl), CO-(C$_1$–C$_6$)-alkyl, CHO, CO-phenyl, —NH$_2$, —N=C(CH$_3$)$_2$, -(pyrrolidin-1-yl), -(piperidin-1-yl), -(morpholin-4-yl), -(piperazin-1-yl) or -(4-methylpiperazin-1-yl), or NR6R7 is a ring selected from the group consisting of pyrrolidine, piperidine, morpholine, piperazine, 4-methylpiperazin-1-yl, 4-benzylpiperazin-1-yl and phthalimidyl;

and its physiologically tolerated salts.

4. A pharmaceutical composition comprising a compound as claimed in claim 1 and a pharmaceutically acceptable carrier.

5. The pharmaceutical composition of claim 4 further comprising one or more anorectic active ingredients.

6. A method for the treatment of obesity comprising administering an obesity treating effective amount of a pharmaceutical composition of claim 4 to a patient in need thereof.

7. A method for the treatment of type II diabetes comprising administering a diabetes treating effective amount of a pharmaceutical composition of claim 4 to a patient in need thereof.

8. The method of claim 6, further comprising administering at least one other anorectic active ingredient for the treatment of obesity.

9. The method of claim 7, further comprising administering at least one other anorectic active ingredient for the treatment of type II diabetes.

10. A process for preparing a pharmaceutical comprising admixing a compound as claimed in claim 1 with a pharmaceutically suitable carrier and converting this mixture into a form suitable for administration.

11. A pharmaceutical composition comprising a compound as claimed in claim 2 and a pharmaceutically acceptable carrier.

12. The pharmaceutical composition of claim 11 further comprising one or more anorectic active ingredients.

13. A method for the treatment of obesity comprising administering an obesity treating effective amount of a pharmaceutical composition of claim 11 to a patient in need thereof.

14. A method for the treatment of type II diabetes comprising administering a diabetes effective amount of a pharmaceutical composition of claim 11 to a patient in need thereof.

15. The method of claim 13, further comprising administering at least one other anorectic active ingredient for the treatment of obesity.

16. The method as claimed in claims 14, further comprising administering at least one other anorectic active ingredient for the treatment of type II diabetes.

17. A process for preparing a pharmaceutical comprising admixing a compound as claimed in claim 2 with a pharmaceutically suitable carrier and converting this mixture into a form suitable for administration.

18. A pharmaceutical composition comprising a compound as claimed in claim 3 and a pharmaceutically acceptable carrier.

19. The pharmaceutical composition of claim 18 further comprising one or more anorectic active ingredients.

20. A method for the treatment of obesity comprising administering an obesity treating effective amount of a pharmaceutical composition of claim 18 to a patient in need thereof.

21. A method for the treatment of type II diabetes comprising administering a diabetes treating effective amount of a pharmaceutical composition of claim 18 to a patient in need thereof.

22. The method as claimed in claims 20, further comprising administering at least one other anorectic active ingredient for the treatment of obesity.

23. The method as claimed in claims 21, further comprising administering at least one other anorectic active ingredient for the treatment of type II diabetes.

24. A process for preparing a pharmaceutical comprising admixing a compound as claimed in claim 3 with a pharmaceutically suitable carrier and converting this mixture into a form suitable for administration.

* * * * *